(12) United States Patent
Bolognia et al.

(10) Patent No.: US 11,712,516 B2
(45) Date of Patent: Aug. 1, 2023

(54) FLUID DELIVERY DEVICE

(71) Applicant: Analog Devices, Inc., Norwood, MA (US)

(72) Inventors: David Frank Bolognia, Charlestown, MA (US); Brian Hall, North Andover, MA (US)

(73) Assignee: Analog Devices, Inc., Norwood, MA (US)

( * ) Notice: Subject to any disclaimer, the term of this patent is extended or adjusted under 35 U.S.C. 154(b) by 471 days.

(21) Appl. No.: 16/851,798

(22) Filed: Apr. 17, 2020

(65) Prior Publication Data
US 2021/0322681 A1  Oct. 21, 2021

(51) Int. Cl.
*A61M 5/148*  (2006.01)
*A61M 5/315*  (2006.01)
*A61M 5/142*  (2006.01)
*A61M 5/145*  (2006.01)

(52) U.S. Cl.
CPC ...... *A61M 5/1483* (2013.01); *A61M 5/14244* (2013.01); *A61M 5/14593* (2013.01); *A61M 5/31586* (2013.01); *A61M 2005/14204* (2013.01); *A61M 2005/14513* (2013.01); *A61M 2205/0272* (2013.01); *A61M 2205/3334* (2013.01)

(58) Field of Classification Search
CPC ............ A61M 5/1483; A61M 5/14593; A61M 5/14244; A61M 2005/14513
See application file for complete search history.

(56) References Cited

U.S. PATENT DOCUMENTS

| | | |
|---|---|---|
| 2,729,976 A | 1/1956 | Laub |
| 4,335,835 A | 6/1982 | Beigler et al. |
| 4,587,843 A | 5/1986 | Tokura et al. |
| 4,688,424 A | 8/1987 | Handtmann et al. |
| 5,073,094 A | 12/1991 | Dorman et al. |
| 5,222,395 A | 6/1993 | Matubara et al. |
| 5,527,288 A | 6/1996 | Gross et al. |
| 5,792,952 A | 8/1998 | Ritchart |
| 5,831,159 A | 11/1998 | Renger |
| 6,537,437 B1 | 3/2003 | Galambos et al. |
| 6,607,495 B1 | 8/2003 | Shalak et al. |
| 6,699,234 B2 | 3/2004 | Yeh |
| 6,889,559 B2 | 5/2005 | Gimson |

(Continued)

FOREIGN PATENT DOCUMENTS

| | | |
|---|---|---|
| EP | 3616737 A2 | 3/2020 |
| GB | 1452104 | 10/1976 |

(Continued)

OTHER PUBLICATIONS

International Search Report and Written Opinion in International Application No. PCT/US2021/027412, dated Aug. 13, 2021.

*Primary Examiner* — Jenna Zhang
(74) *Attorney, Agent, or Firm* — Knobbe, Martens, Olson & Bear, LLP

(57) ABSTRACT

A substance delivery device is disclosed. The substance delivery device includes a lever that includes a drive arm that is rotatable about a pivot. The substance delivery device also includes a pump that has a deformable chamber. The deformable chamber is configured to rotate the drive arm about the pivot towards a container so as to deform the container to drive a fluid substance from the container.

15 Claims, 15 Drawing Sheets

(56) References Cited

U.S. PATENT DOCUMENTS

| | | |
|---|---|---|
| 9,132,231 B2 | 9/2015 | Gross et al. |
| 9,492,614 B2 | 11/2016 | Kamen et al. |
| 9,616,171 B2 | 4/2017 | Qin et al. |
| 9,661,408 B2 | 5/2017 | Kierse et al. |
| 2006/0079862 A1* | 4/2006 | Genosar .............. A61M 5/1454 604/890.1 |
| 2011/0060280 A1 | 3/2011 | Caffey et al. |
| 2011/0275996 A1* | 11/2011 | Gyory ............... A61M 5/16877 604/131 |
| 2014/0135699 A1* | 5/2014 | Gyory .................. A61M 5/148 604/151 |
| 2016/0105737 A1 | 4/2016 | Kierse et al. |
| 2017/0232189 A1 | 8/2017 | Qin et al. |
| 2019/0126018 A1 | 5/2019 | Browd et al. |
| 2019/0135614 A1 | 5/2019 | Kierse et al. |
| 2019/0184095 A1 | 6/2019 | Kim et al. |
| 2019/0255254 A1 | 8/2019 | Wilmont et al. |
| 2021/0196884 A1 | 7/2021 | Kim et al. |

FOREIGN PATENT DOCUMENTS

| | | |
|---|---|---|
| WO | WO 95/13839 | 5/1995 |
| WO | WO 2020/040519 A1 | 2/2020 |

* cited by examiner

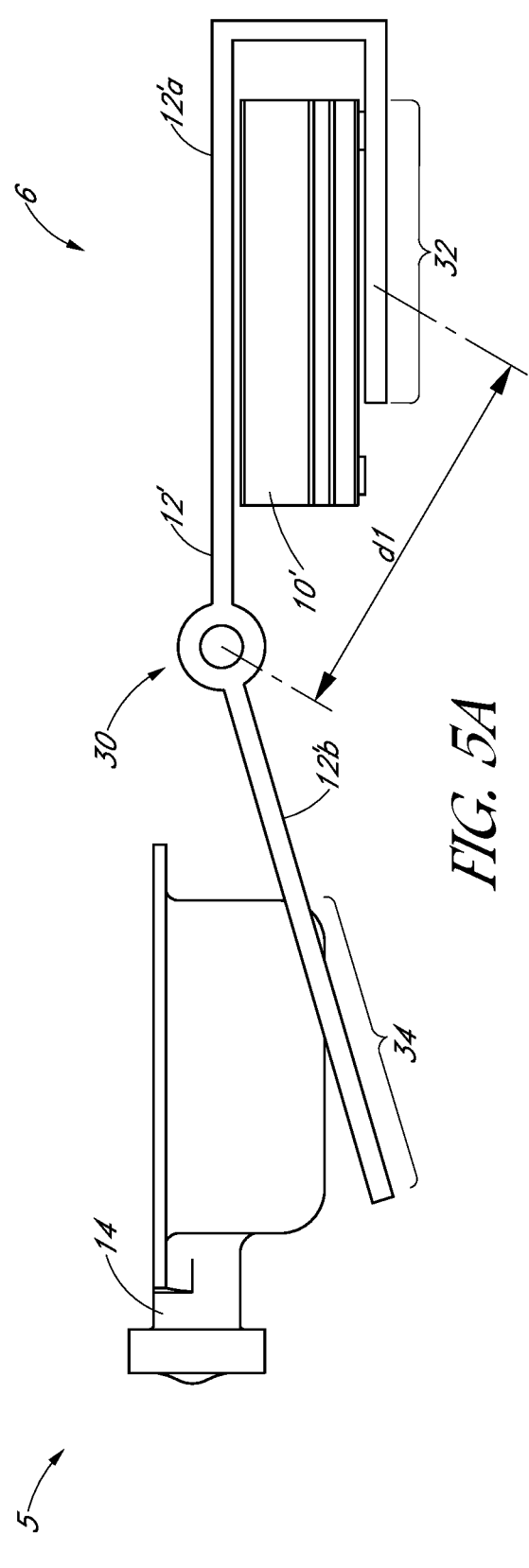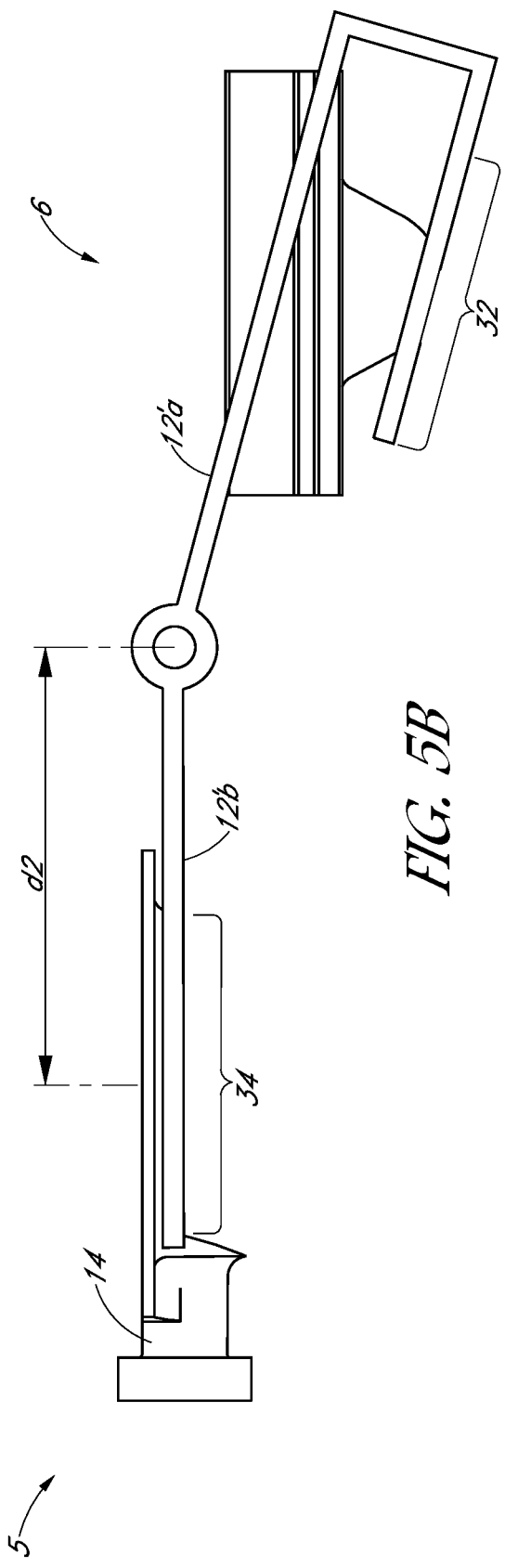
FIG. 5A
FIG. 5B

FLUID DELIVERY DEVICE

BACKGROUND

Field

The field relates to substance delivery devices and, in particular, to fluid delivery devices.

Description of the Related Art

Substance delivery systems can deliver a substance, e.g., a fluid substance, from one location to another. An example of a substance delivery system is a drug delivery system. In a drug delivery system, a drug can be stored in one place and the drug can be delivered to a patient's body. A substance delivery system can include a mechanical pump that delivers a substance from one place to another.

SUMMARY

In one aspect, a substance delivery device is disclosed. The substance delivery device includes a lever that includes a drive arm that is rotatable about a pivot. The substance delivery device also includes a pump that has a deformable chamber. The deformable chamber is configured to rotate the drive arm about the pivot towards a container so as to deform the container to drive a fluid substance from the container.

In one embodiment, the lever further includes an effort arm that extends from the pivot. The pivot can be positioned between the drive arm and the effort arm. The deformable chamber can move the drive arm and the effort arm.

In one embodiment, the pump is an electroosmotic (EO) pump or an electrochemical (EC) pump.

In one embodiment, the pump and the lever are arranged such that an expansion volume of the deformable chamber is smaller than a volume of the fluid substance driven. The volume of the fluid substance can be at least twice the expansion volume. The expansion volume can be 25 micro litters ($\mu L$) to 100 $\mu L$.

In one embodiment, the device further includes a package substrate that has one or more electrical interconnects. The lever and the pump can be electrically coupled to the package substrate.

In one embodiment, a substance delivery system includes the substance delivery device that is coupled to a support. The substance delivery system can also include the substance container that is coupled to the support. The substance delivery system and the substance container can be coupled to a same side of the support.

In one aspect, a substance delivery device is disclosed. The substance delivery device includes a lever that has a fulcrum, an effort region, and a load region. the substance delivery device also include an electroosmotic (EO) pump that has an deformable chamber. The EO pump is configured to apply an effort force to the effort region of the lever thereby causing the effort region and the load region of the lever to move. The load region is positioned to apply a load force to a container that includes a fluid substance.

In one embodiment, the lever includes a drive arm that extends from the fulcrum. The drive arm can include the load region. The lever can include an effort arm that extends from the fulcrum. The effort arm can include the effort region. The fulcrum can be positioned between the effort region and the load region.

In one embodiment, the lever includes a drive arm that extends from the fulcrum. The drive arm can include the load region. The drive arm can include the effort region. The effort region can be positioned between the load region and the fulcrum.

In one embodiment, the EO pump further includes a second deformable chamber, a porous electrode that is positioned between the deformable chamber and the second chamber, and a porous membrane that is positioned between the deformable chamber and the second chamber. The deformable chamber and the second deformable chamber can be in fluid communication.

In one embodiment, the pump and the lever are arranged such that an amplified displacement of the lever at the load region in response to the application of the effort force is greater than a displacement of the lever at the effort region in response to the application of the effort force. The amplified displacement of the lever at the load region can be at least twice the displacement of the lever at the effort region.

In one embodiment, the pump causes the deformable chamber to expand by between about 25 micro litters ($\mu L$) and 100 $\mu L$.

In one embodiment, the device further includes a package substrate that has electrical interconnects. The lever and the pump can be electrically coupled to the package substrate.

In one aspect, a substance delivery device is disclosed. The substance delivery device includes a lever that has a fulcrum, an effort region, and a load region. The lever is coupled to a substrate. The substance delivery device also include an electroosmotic (EO) pump that is configured to apply an effort force to the effort region of the lever to cause the effort region and the load region of the lever to move. The load region positioned to apply a load force to a container that includes a fluid substance to drive the fluid substance from the container.

In one embodiment, the EO pump comprises a deformable chamber, the deformable chamber configured to deform and apply the effort force to the effort region of the lever.

In one embodiment, the EO pump and the lever are arranged such that an amplified displacement of the lever at the load region in response to the application of the force is greater than a displacement of the lever at the effort region in response to the application of the force. The amplified displacement can be at least twice the displacement.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

FIG. 5A is a schematic side view of a substance delivery system in a first state according to another embodiment.

FIG. 5B is a schematic side view of the substance delivery system illustrated in FIG. 5A in a second state.

DETAILED DESCRIPTION

Figure 1A:
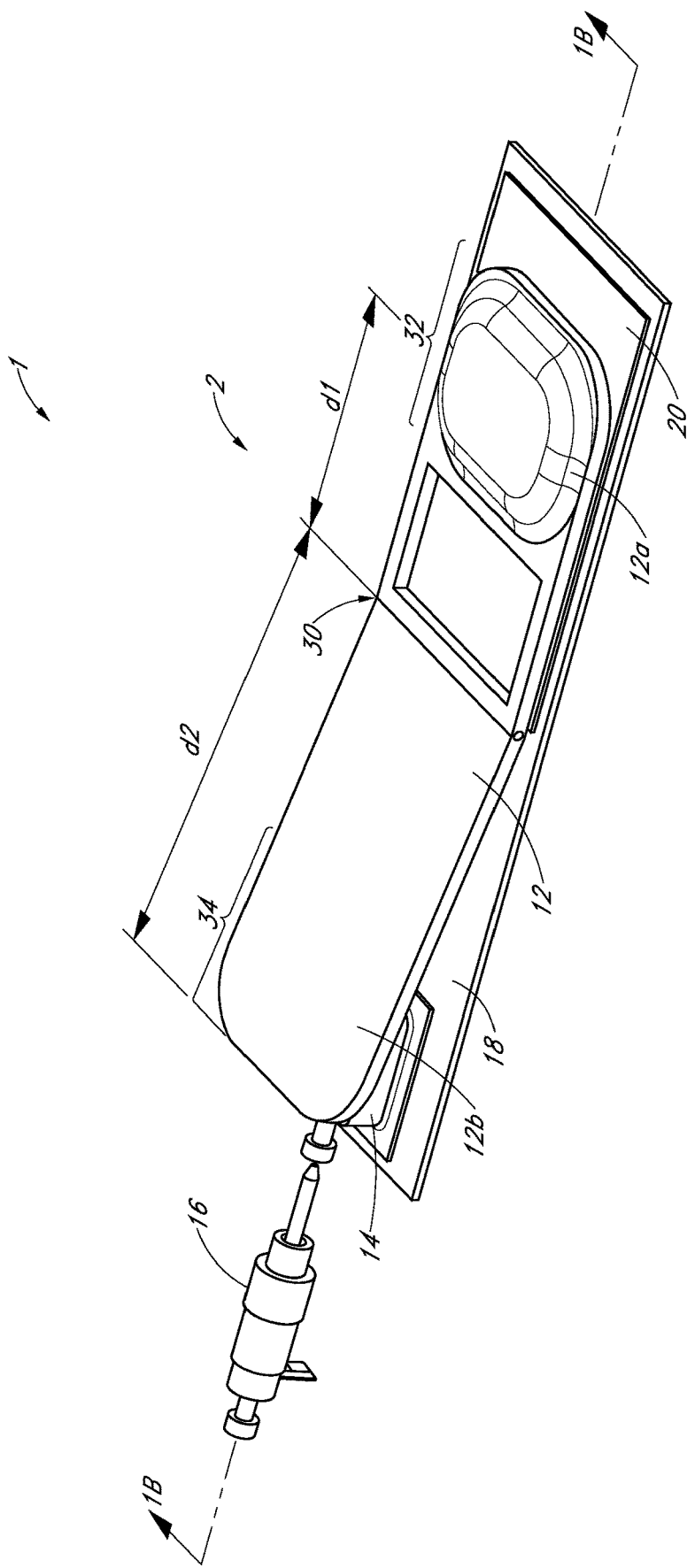
FIG. 1A is a schematic perspective view of a substance delivery system in a first state according to one embodiment.

Substance delivery systems, for example, a drug delivery system, can be used to deliver a fluid substance (e.g., a drug) disposed in a reservoir to a target location (e.g., inside a patient's vasculature or analysis equipment). The drug can include, for example, insulin for treating diabetes, an anti-nausea drug for chemotherapy, etc. The drug delivery system can include a drug delivery device that includes a mechanical pump that creates force to deliver the drug from the reservoir to the target location. The drug delivery device can drive the drug from the reservoir continuously or periodically. The drug delivery device can drive the drug from the reservoir with a continuous increment or a plurality of discrete increments. However, conventional mechanical pumps can be relatively large and can require relatively high power to operate. Therefore, it can be undesirable for certain applications, such as for use in a wearable device. When small pumps are used, it can be challenging to precisely and effectively deliver a desired amount of a drug.

Various embodiments disclosed herein relate to a substance delivery device that includes a pump that operates with a relatively low power. For example, the pump can comprise an electroosmotic (EO) pump, an electrochemical (EC) pump, or a piezoelectric pump. The pump can include an expandable or deformable chamber configured to receive and contain a solution (e.g., an electrolyte). The expandable or deformable chamber can include an elastic or expandable diaphragm that can expand in response to a pressure difference in the chamber caused by a movement or a volumetric expansion of the solution in the chamber. The solution can comprise any suitable solution. For example, the solution can comprise water ($H_2O$). The expansion of the diaphragm can be used to drive a fluid substance (e.g., a drug) out of the reservoir. When the expansion of the diaphragm is directly applied to the substance in the reservoir, in some embodiments a volume of the substance forced out from the reservoir can be the same or generally similar to a volume of expansion of the diaphragm. In other embodiments, the volume of the substance driven out of the reservoir can differ from the expanded volume of the diaphragm.

Various embodiments disclosed herein also relate to a substance delivery device that includes a mechanical structure that amplifies a movement caused by the pump (e.g., the volume of expansion of the diaphragm). The mechanical structure can include a lever having a fulcrum, an effort region, and a load region. Relative positions of the fulcrum, the effort, and the load can be fixed. Force (the movement caused by the pump) can be applied to the effort region of the lever, thereby causing the effort region of the lever to move. The movement of the effort region can be conveyed to the load region of the lever. The lever can have a first state (an initial position) and a second state (displaced position). The first state can be referred to a state where no force by the pump is applied to the effort region, and the second state can be referred to a state where force is applied to the effort region by the pump. A displacement of the lever at the effort region between the first state and the second state can be amplified through the lever such that an amplified displacement of the lever at the load region between the first state and the second state is greater than the displacement of the lever at the effort region.

In some aspects, a substance delivery device is disclosed. The device can include a lever having a fulcrum, an effort region, and a load region, and a pump configured to cause movement of the lever. In some embodiments, the lever can comprise an arm (a drive arm) that extends from the fulcrum. In some other embodiments, the lever can comprise a plurality of arms (the drive arm and an effort arm). The load region can be located at a portion of the drive arm, and the effort region can be located at another portion of the drive arm or a portion of the effort arm. The pump can comprise an electroosmotic (EO) pump, an electrochemical (EC) pump, or a piezoelectric pump. The pump can apply force to the effort region of the lever thereby causing the lever to move. A displacement of the lever at the effort region between a first state and a second state can be amplified through the lever, such that an amplified displacement of the lever at the load region between the first state and the second state is greater than the displacement of the lever at the effort region. The pump can be mounted to a substrate. The fulcrum of the lever can be movably coupled to the substrate. The effort region and the load region can rotate about the fulcrum. The fulcrum of the lever can be coupled to the substrate by way of a hinge.

A substance delivery system can include the device. The substance delivery system can also include a substance reservoir (e.g., a substance pod). The substance reservoir can be coupled to a substrate. For example, the substrate can comprise a holder and the substance reservoir can be inserted into the holder. The substance reservoir can be configured to receive a substance (e.g., a drug). The movement of the lever caused by the pump can be applied to the substance reservoir thereby forcing the substance out from the substance reservoir. The system can also include a conduit (e.g., a tube) that can convey the substance from the substance reservoir to a target location. The system can also include a flow meter that monitors a flow rate and a flow amount of the substance forced out from the reservoir. The flow meter can be associated with the pump to manage the flow rate and total volume of the substance to deliver. The system can also include a control valve. The control valve can function as, for example, a shutoff valve and/or a check valve. When the control valve functions as a shutoff valve, it can close the flow of the substance. When the control valve functions as a check valve, it can prevent or mitigate a backflow of the substance. The flow meter can be associated with the control valve to manage the operations of the shutoff valve and the check valve.

The substance delivery system can also include electronics (e.g., a controller) that can control operation of the substance delivery system. For example, the substance delivery device, the flow meter, and the shutoff valve can connect to the controller. The substance delivery device, the flow meter, the shutoff valve, and the controller can at least partially define a substance delivery module.

Figure 1B:
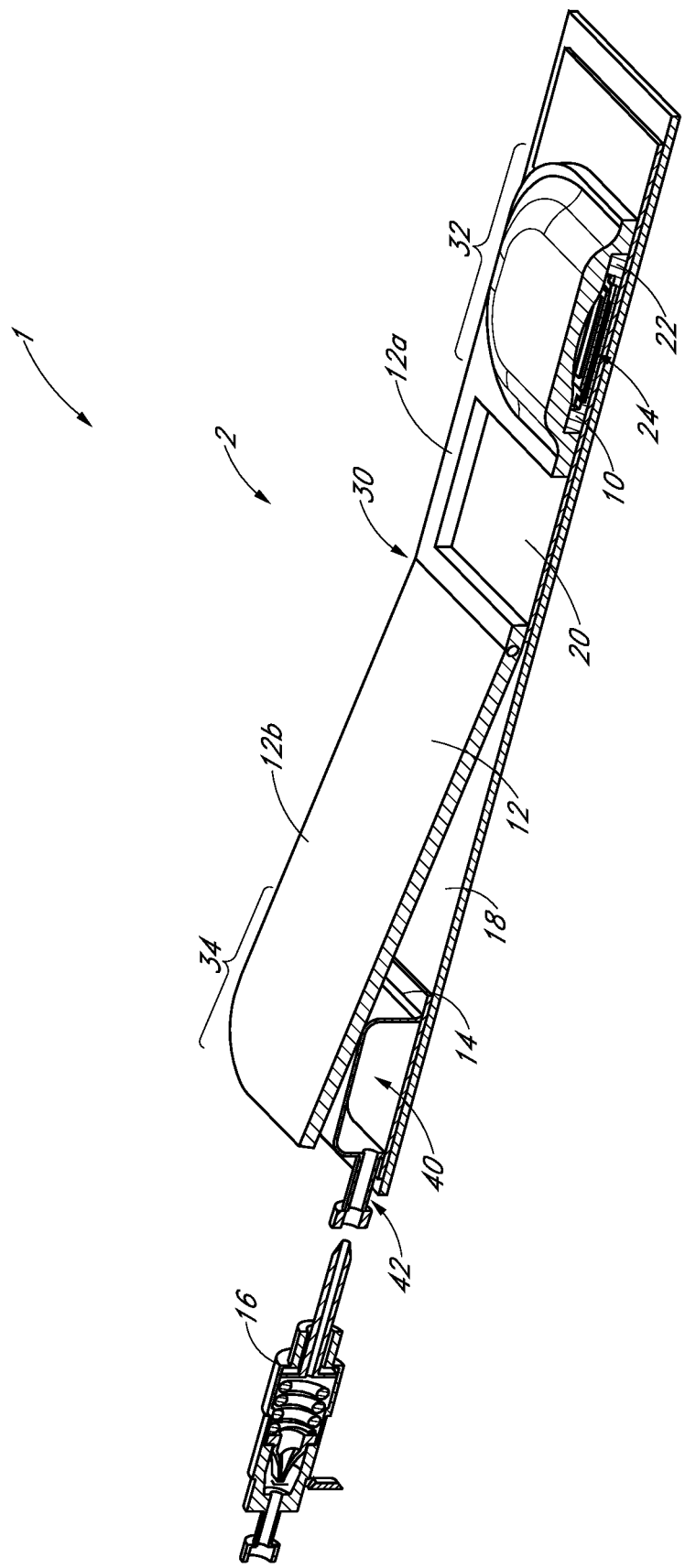
FIG. 1B is a schematic cross-sectional view of the substance delivery system illustrated in FIG. 1A.
Figure 2A:
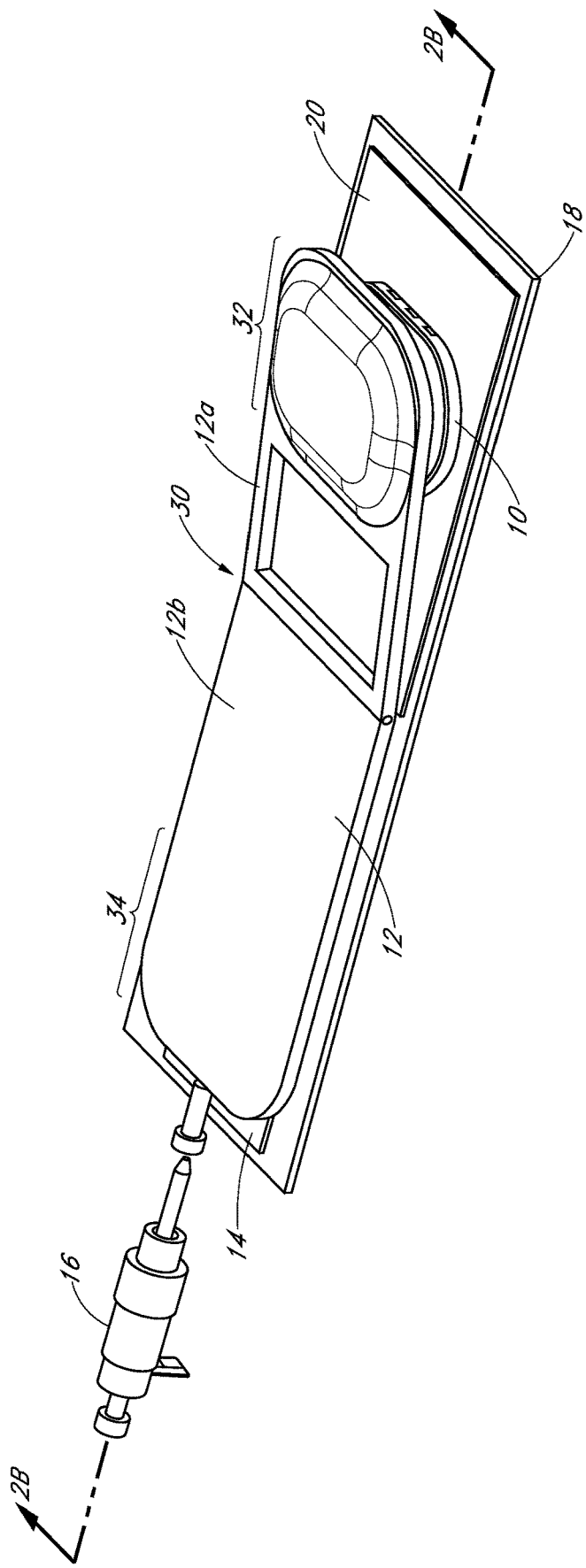
FIG. 2A is a schematic perspective view of the substance delivery system illustrated in FIG. 1A in a second state.
Figure 2B:
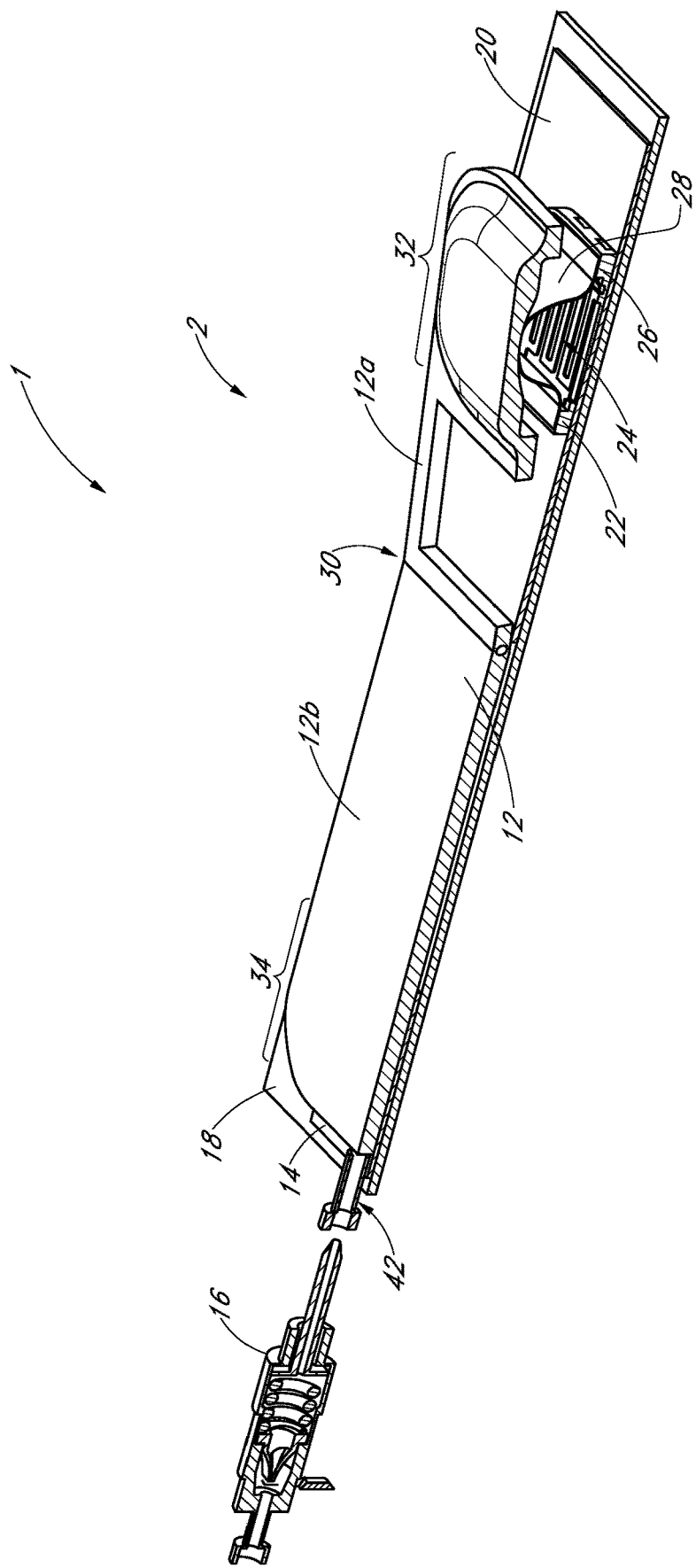
FIG. 2B is a schematic cross-sectional view of the substance delivery system illustrated in FIG. 2A.

FIG. 1A is a schematic perspective view of a substance delivery system 1 in a first state according to one embodiment. FIG. 1B is a schematic cross-sectional view of the substance delivery system 1 illustrated in FIG. 1A. FIG. 2A is a schematic perspective view of the substance delivery system 1 illustrated in FIG. 1A in a second state. FIG. 2B is a schematic cross-sectional view of the substance delivery system 1 illustrated in FIG. 2A.

The substance delivery system 1 can include a substance delivery device 2. The substance delivery device 2 can comprise a pump 10 and a lever 12. The substance delivery system 1 can include a container 14 (e.g., a drug pod) configured to receive and store a fluid substance (e.g., a drug). The substance delivery system 1 can include a needle subassembly 16 that is configured to couple to the container 14. The substance delivery system can include a support 18. The substance delivery device 2 and the container 14 can be mounted to the support 18. The pump 10 and the container 14 can be mounted to a same side of the support 18. The pump 10 and the container 14 can be spaced apart. For example, the pump 10 and the container 14 can be spaced laterally along a longitudinal direction of the support.

In some embodiments, the pump 10 (see FIG. 1B-2B) can be mounted to a substrate 20. The substrate 20 can be coupled or mounted to the support 18. In some embodiments, the substrate 20 can comprise interconnects (not illustrated) such as one or more conductive traces formed in or on the substrate 20. For example, the substrate 20 can comprise a laminate substrate (such as a printed circuit board, or PCB) in some embodiments. The interconnect can be electrically connected with the pump 10. In some applications, it can be beneficial to use a pump that can be operated with relatively low power in the substance delivery system 1. The pump 10 illustrated in FIGS. 1A-2B comprises an electrochemical (EC) pump. However, in other embodiments, the pump 10 can comprise an electroosmotic (EO) pump, piezoelectric pump, or any other suitable pumps. The pump 10 can comprise a housing 22 that at least partially defines a chamber 24, electrodes 26, and a diaphragm 28. The chamber 24 can receive and contain a solution such as an electrolyte material. During operation, a potential difference can be applied through the one or more interconnects of the substrate 20 across the electrodes 26, which may be interdigitated in some embodiments. The solution in the chamber 24 can react in response to the applied potential difference. The diaphragm 28 can comprise an elastic or flexible material. Therefore the chamber 24 can comprise an expandable or deformable chamber. The diaphragm 28 can expand in response to the reaction in the chamber 24. Additional details of electrochemical (EC) devices may be found at least in U.S. Provisional Application No. 62/867,703, the entire contents of which are incorporated by reference herein in their entirety and for all purposes.

The lever 12 has a pivot or fulcrum 30, an effort arm 12a that comprises an effort region 32, and a drive arm 12b that comprises a load region 34. The effort region 32 is an approximate location at which an effort force is effectively applied, and the load region 34 is an approximate location at which a load force is effectively applied. In some embodiments, relative positions of the fulcrum 30, the effort region 32, and the load region 34 can be fixed relative to each other.

In some embodiments, the effort region 32 and the load region 34 of the lever can rotate together about the fulcrum 30. The pump 10 can be positioned at the effort region 32 of the lever 12 and the container 14 can positioned at the load region 34 of the lever 12, so as to provide a mechanical advantage for the lever 12. In the first state illustrated in FIGS. 1A and 1B, the pump 10 does not apply an external force to the lever 12. In other words, the pump 10 does not apply an external force to the container 14 in the first state that would be sufficient to deform or collapse the container 14. In the second state illustrated in FIGS. 2A and 2B, the pump 10 applies a force to the effort region 32 of the lever 12 to cause the lever 12 to move relative to the position of the lever 12 in the first state. For example, the pump 10 causes the load region 34 to pivot about the fulcrum 30 so as to apply a force to the container 14 through the lever 12. As explained herein, the applied force may be sufficient to deform or collapse the container 14 to drive a fluid substance (e.g. a drug) out of the container 14.

The effort region 32 of the lever 12 can be designed to at least partially conform with a shape of the pump 10. In some embodiments, the effort region 32 can comprise a recessed portion, and the pump 10 can be at least partially disposed in the recessed portion. In some embodiments, the pump 10 can be fully disposed in the recessed portion such that a surface of the lever 12 is flush with a surface of the pup 10. The pump 10 can apply force in a direction generally perpendicular with a surface of the support 18.

A distance from the fulcrum 30 and the effort region 32 can be referred to as an effort distance d1, and a distance from the fulcrum 30 to the load region can be referred as a load distance d2. In some embodiments, the effort distance d1 can be greater than the load distance d2. In some other embodiments, the load distance d2 can be greater than the effort distance d1. When the effort distance d1 is greater than the load distance d2 in the substance delivery device 2, the pressure applied at the effort region 32 can be amplified at the load region 34. When the load distance d2 is greater than the effort distance d1 in the substance delivery device 2, the pressure applied at the effort region 32 can be decreased at the load region 34. In some embodiments, an effort pressure applied to the effort region can be amplified through the lever 12 to create a load pressure at the load region that is 1.5 to 5 times the effort pressure. In some embodiments, the load pressure can be, for example, 2 to 5 times the effort pressure, for example, 2 to 4 times the effort pressure, for example, 2 times the effort pressure. In some embodiments, the effort pressure can be in a range of, for example, 1 psi to 7 psi, in a range of, for example, 4 psi to 7 psi, in a range of, for example, 1 psi to 5 psi, or in a range of, for example, 4 psi to 5 psi. In some embodiments, the load pressure can be in a range from, for example, 5 psi to 15 psi, in a range from, for example, 7 psi to 20 psi, in a range from, for example, 5 psi to 15 psi, or in a range from, for example, 7 psi to 15 psi. In some embodiments the pump 10 can apply the effort pressure of about 7.5 pound per square inch (psi) at the effort region 32. In such embodiments, the load pressure at the load region 34 can be about 15 psi.

In some embodiment, a displacement of the lever 12 at the effort region 32 between the first state and the second state (e.g., by way of a pivoting motion of the effort region 32) can be amplified through the lever 12 such that an amplified displacement of the lever 12 at the load region 34 between the first state and the second state is greater than the displacement of the lever 12 at the effort region 32. A relationship between the displacement and the applied displacement can be modified at least by adjusting the effort distance d1 and the load distance d2. In some embodiments, the pump 10, lever 12, and the container 14 can be relatively positioned such that the amplified displacement of the lever 12 at the load region 34 is 1.5 times greater than the displacement of the lever 12 at the effort region 32. In such embodiment, a displacement ratio of the displacement of the lever 12 at the effort region 32 and the amplified displacement of the lever 12 at the load region 34 is 1.5. In some embodiments, displacement ratio of the displacement of the lever 12 at the effort region 32 and the amplified displacement of the lever 12 at the load region 34 can be in a range from, for example, 1.5 to 5, in a range from, for example, 1.5 to 3, in a range from, for example, 2 to 5, or in a range from, for example, 2 to 3.

In the illustrated substance delivery device 2, the pivot or fulcrum 30 of the lever 12 is disposed between the effort region 32 and the load region 34. However, in some embodiments, the relative positioned of the fulcrum 30, the effort region 32, and the load region 34 can be varied. For example, the load region 34 can be between the fulcrum 30 and the effort region 32, or the effort region 32 can be between the fulcrum 30 and the load region 34 (see FIGS. 3A-4B).

The container 14 can comprise a reservoir 40 and an access port 42. When the force from the pump 10 is applied to the container 14 through the lever 12 (e.g., through the downwardly-pivoting load region 34), the fluid substance in the reservoir 40 can be forced out through the access port 42. For example, the container 14 can comprise a flexible material sized and selected to deform or collapse upon application of a downward force by the downwardly-pivoting load region 34. In some embodiments, the substance can be loaded into the reservoir 40 through the access port 42. In some embodiments, the substance can comprise drug such as, for example, insulin for treating diabetes, an anti-nausea drug for chemotherapy, etc. In some embodiments, the reservoir 40 can have a volume (substance capacity) in a range from, for example, 100 micro litters (μL) to 500 μL, in a range from, for example, 150 micro μL to 500 μL, in a range from, for example, 100 micro μL to 300 μL, or in a range from, for example, 150 micro μL to 300 μL.

The needle subassembly 16 can be configured to fluidly couple to the container 14 and a conduit (not illustrated) to convey the substance from the reservoir 40 to a target location. The target location can be, for example, inside of a patient's body (for example, inside the vascular system of the patient), or an external device (for example, analysis equipment configured to analyze or test blood, drugs, or other fluids). In some embodiments, the needle subassembly 16 and the container 14 can be easily coupled and/or decoupled, for example, by way of a press fit or snap fit connection.

In some embodiments, the support 18 can include a holder (not illustrated) that can receive the container 14. In such embodiments, the container 14 can be coupled to the support 18 by way of the holder. The holder can enable the substance delivery system 1 to relatively easily couple and/or decouple the container 14. In some embodiments, the support 18 can include an interconnect (not illustrated) such as a conductive trace formed in or on the support 18. However, in some other embodiments, the support 18 can be electrically inactive.

In some applications the substance delivery system 1 can be designed to be used in a wearable device. In one application, the substance delivery system 1 can be a drug delivery system used in a wearable device. In such application, a patient can wear the drug delivery system with a needle inserted through the skin. The wearable device can include electronics that can be programmed to apply voltage to the substance delivery device 2, such that the container 14 is progressively deformed or collapsed over time. As the container 14 is deformed or collapsed, the drug in the container 14 can be incrementally delivered to the patient's body. The substance delivery system 1 can be sufficiently small for everyday use by the patient. In some embodiments, the substance delivery system 1 can be designed such that the substance delivery device 2 and the container 14 are packaged within a dimension of 40 millimeters (mm)×20 mm×10 mm (length×width×height).

Figure 3A:
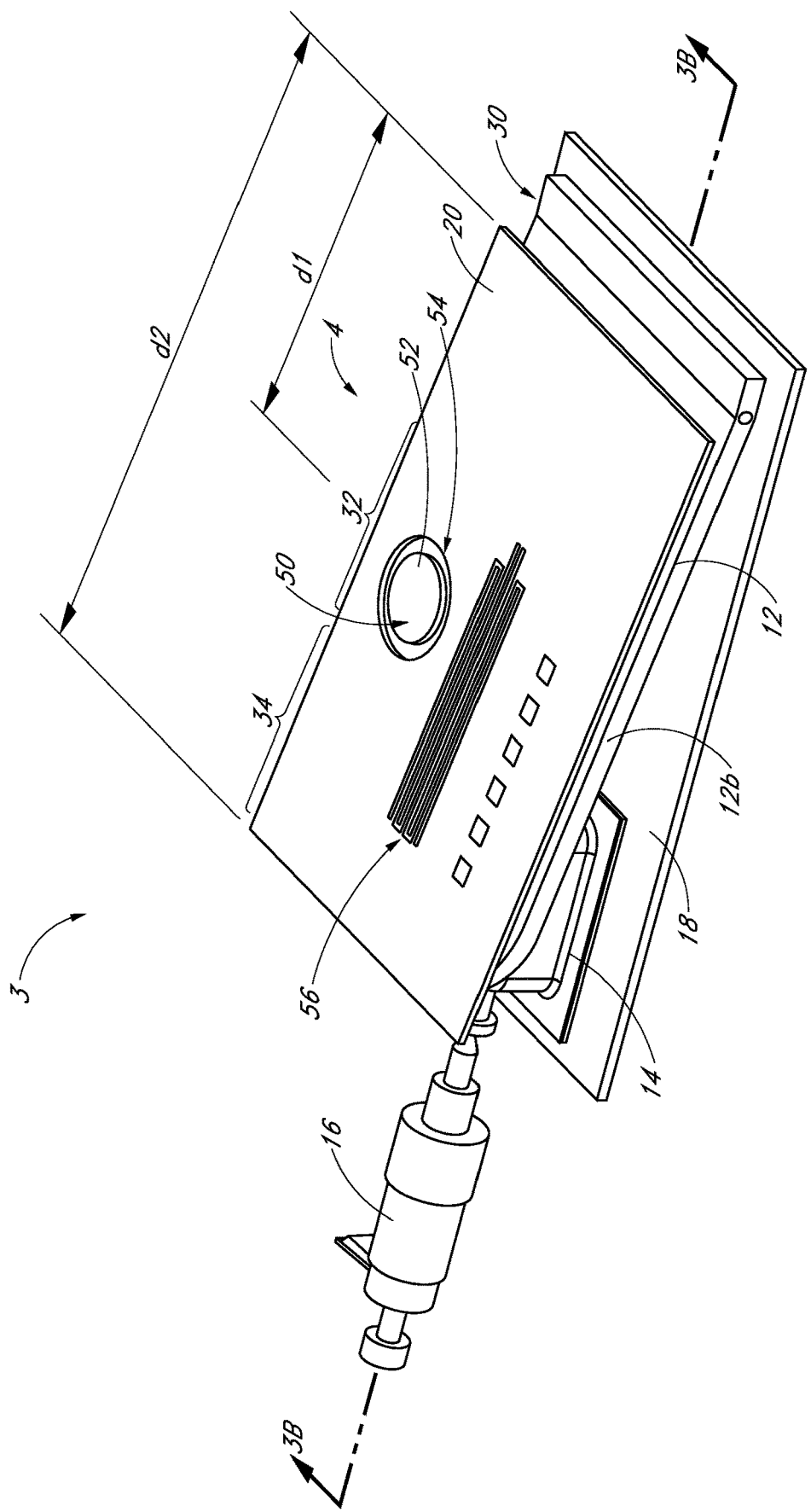
FIG. 3A is a schematic perspective view of a substance delivery system in a first state according to another embodiment.
Figure 3B:
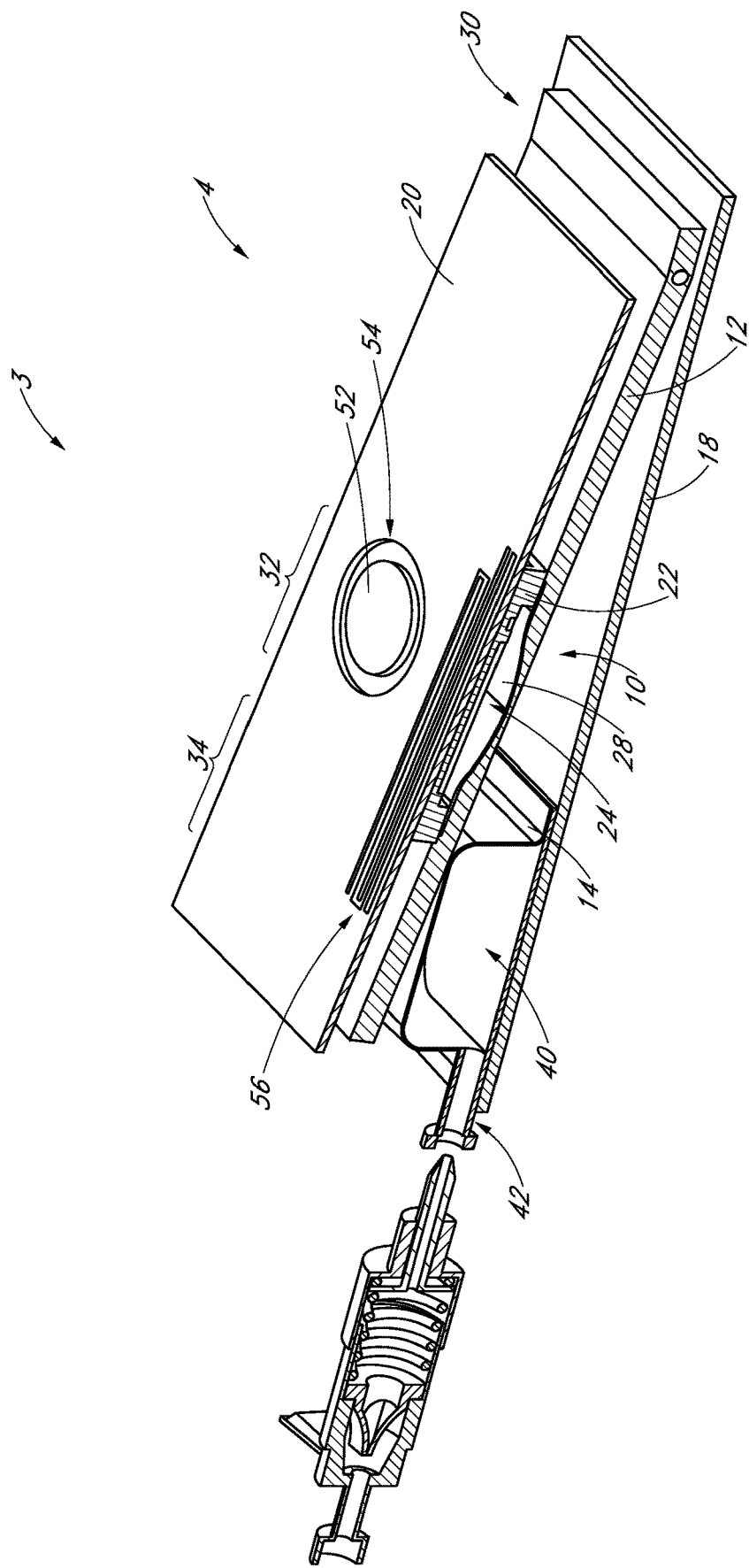
FIG. 3B is a schematic cross-sectional view of the substance delivery system illustrated in FIG. 3A.
Figure 4A:
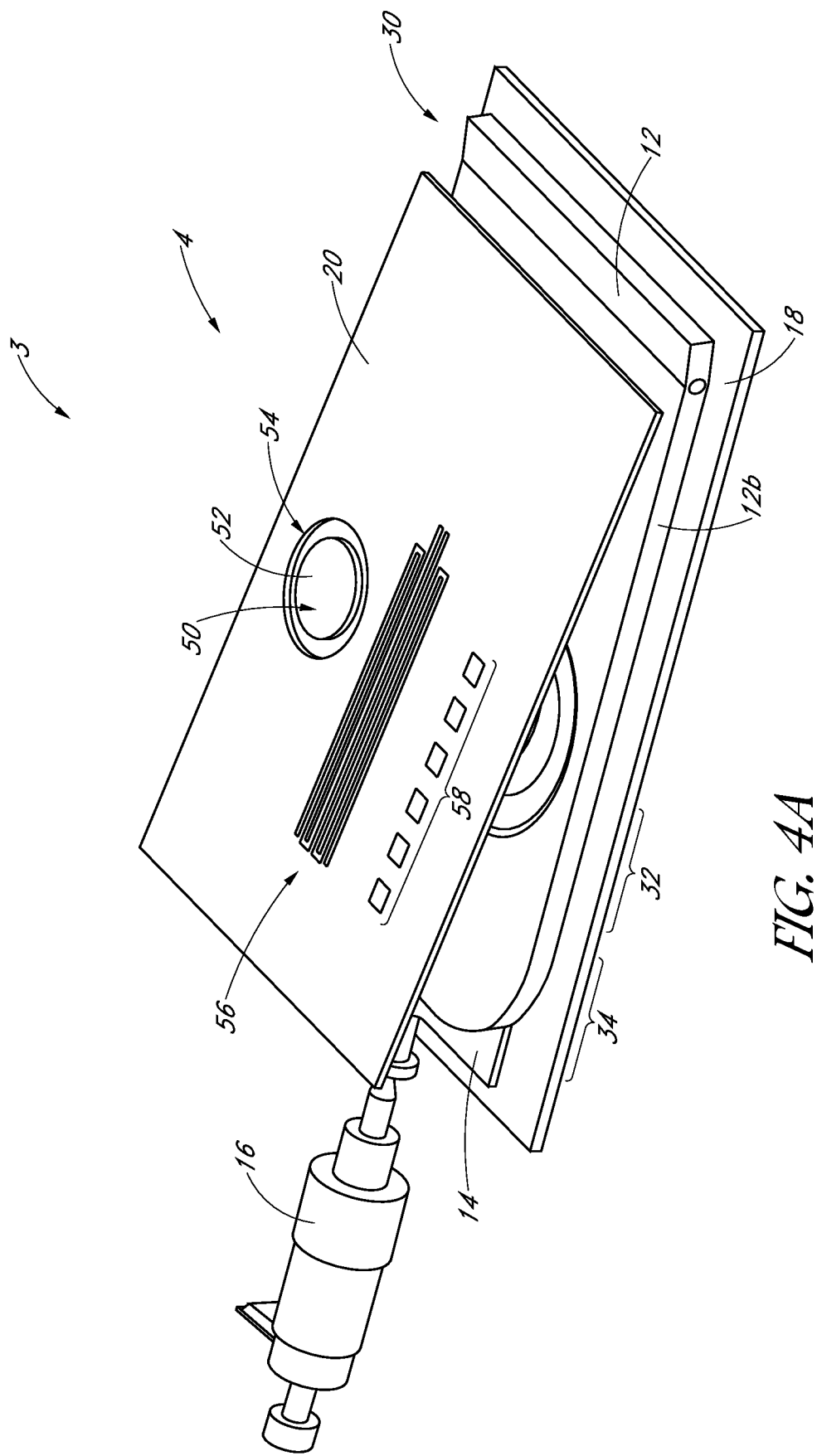
FIG. 4A is a schematic perspective view of the substance delivery system illustrated in FIG. 3A in a second state.
Figure 4B:
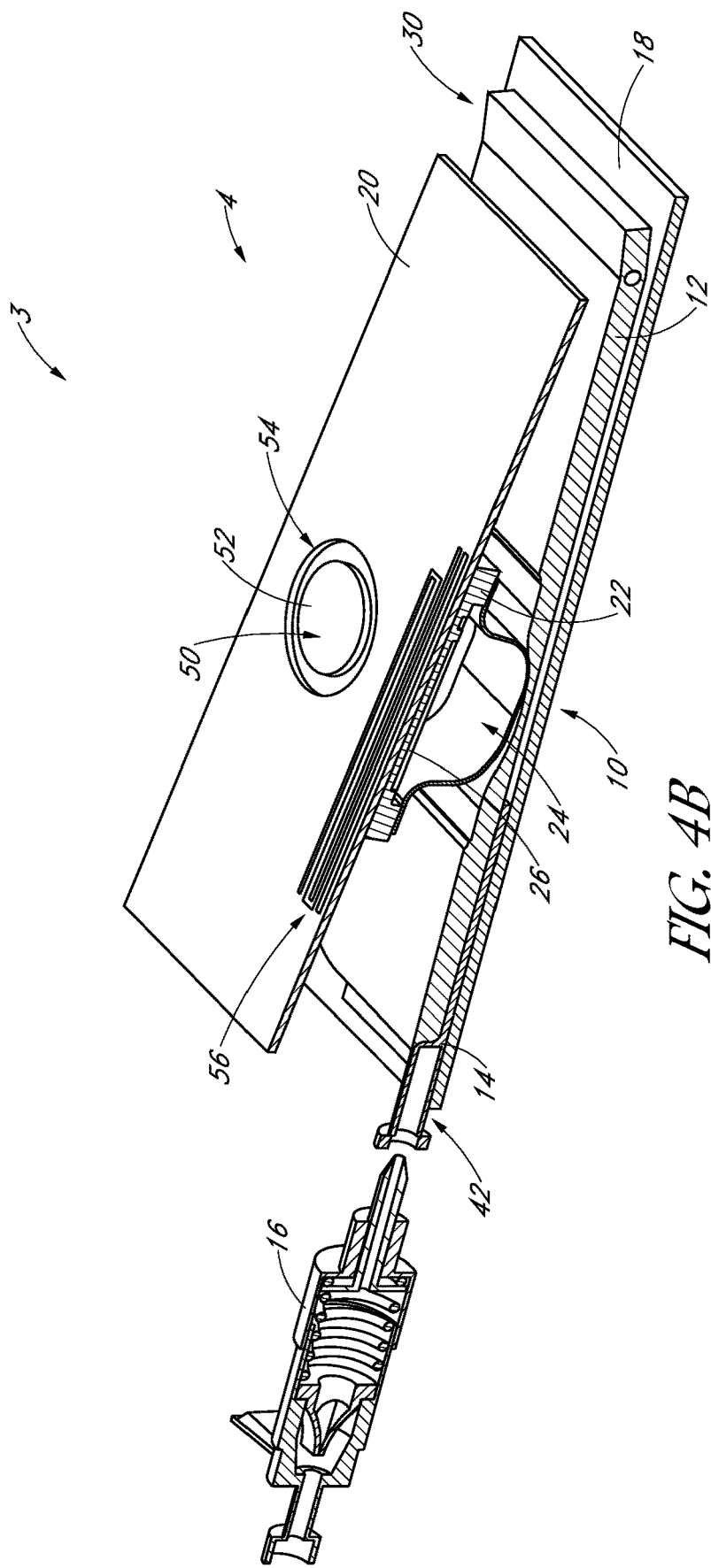
FIG. 4B is a schematic cross-sectional view of the substance delivery system illustrated in FIG. 4A.

FIG. 3A is a schematic perspective view of a substance delivery system 3 in a first state according to one embodiment. FIG. 3B is a schematic cross-sectional view of the substance delivery system 3 illustrated in FIG. 3A. FIG. 4A is a schematic perspective view of the substance delivery system 3 illustrated in FIG. 3A in a second state. FIG. 4B is a schematic cross-sectional view of the substance delivery system 3 illustrated in FIG. 4A. The substance delivery system 3 is generally similar to the substance delivery system 1 illustrated in FIGS. 1A-2B. However, arrangements of the components in the substance delivery systems 1, 3 are different. Unless otherwise noted, components of FIGS. 3A-4B may be the same as or generally similar to like-numbered components of FIGS. 1A-2B.

The substance delivery system 3 can include a substance delivery device 4. The substance delivery device 4 can comprise a pump 10 (see FIGS. 3B and 4B) and a lever 12. In some embodiments, the pump 10 can be coupled to a substrate 20. The substance delivery system 3 can include a container 14 (e.g., a drug pod) configured to receive a fluid substance (e.g., drug). The substance delivery system 3 can include a needle subassembly 16 that is configured to couple to the container 14. The substance delivery system can include a support 18. The substance delivery device 4 and the container 14 can be coupled to the support 18. The substrate 20 can be coupled to a structure (not shown) thereby fixing the relative positions of the pump 10 and the container 14.

The pump 10 can comprise a housing 22 that at least partially defines a chamber 24, electrodes 26, and a diaphragm 28. The chamber 24 can receive a solution such as an electrolyte material. The housing 22 can include a fill hole 50 which can be plugged or sealed with a plug 52. The solution can be supplied into the chamber 24 through the fill hole 50.

In some embodiments, the substrate 20 can include an opening 54 configured to provide access to the fill hole 50 of the housing 22. In some embodiments, the substance 20 can comprise an antenna 56. The antenna 56 can be formed on an outer surface of the substrate 20 to provide wireless communication with an external device. In some embodiments, the substrate 20 comprise contact pads 58. For example, the substrate 20 can be electrically coupled with an external device or system by way of contact pads 58.

Unlike the lever 12 shown in FIG. 1A-2B where the effort region 32 is located at a portion of the effort arm 12a and the load region 34 is located at a portion the drive arm 12b, the arm 12 shown in FIGS. 3A-4B comprises a drive arm 12 that extends from the pivot or fulcrum 30 and such that the drive arm 12 comprises both the effort region 32 and the load region 34. In some embodiments, a distance between the effort region 32 and the fulcrum 30 is shorter than a distance between the load region 34 and the fulcrum 30. In FIGS. 3A-4B, expansion of the chamber 24 imparts an effort force against the effort region 32 of the drive arm 12. The load region 34 of the drive arm 12 in turn imparts a load force on the container 14 to drive the fluid substance from the container 14. The drive arm 12 can accordingly pivot about the pivot or fulcrum 30 in response to the effort force.

In some embodiments, the drive arm 12a disclosed herein can directly or indirectly imparts a load force on the container 14. In some embodiments, the drive arm 12a can contact the container 14 to squeeze or deform the container 14 to drive the fluid substance out from the container 14. In some applications, the effort force can be controlled by tuning the voltage or signal applied to the electrodes of the pump 10. In some embodiments, the load force applied to the container 14 can be tuned in a continuous or analog manner such that any desired force can be applied to the container 14 by adjusting the voltage or signal to the electrodes of the pump 10 appropriately. In some embodiments, the effort force applied to the effort region 32 can be transferred or conveyed to the load region 34 instantaneously.

FIG. 5A is a schematic side view of a substance delivery system 5 in a first state according to one embodiment. FIG. 5B is a schematic side view of the substance delivery system 5 illustrated in FIG. 5A in a second state. Unless otherwise noted, components of FIGS. 5A and 5B may be the same as or generally similar to like-numbered components of FIGS. 1A-4B. Also, any suitable principles and advantages disclosed herein, including those disclosed with respect to FIGS. 1A-4B, can be applied to the substance delivery system 5.

The substance delivery system 5 can include a substance delivery device 6. The substance delivery device 6 can comprise a pump 10' and a lever 12'. Unlike the EC pump of FIGS. 1A-4B above, the pump 10' illustrated in FIGS. 5A and 5B comprises an electroosmotic (EO) pump. However, in other embodiments, the pump 10 can comprise an electrochemical (EC) pump, piezoelectric pump, or any other suitable pumps. The substance delivery system 5 can include a container 14 (e.g., a drug pod) configured to receive a substance (e.g., drug). The substance delivery system 5 can also include a packaging structure (not illustrated) which can package the substance delivery device 5 and the container 14.

As with the lever 12 illustrated in FIGS. 1A-4B, the lever 12' has a fulcrum 30, an effort arm 12'a that comprises an effort region 32, and a drive arm 12'b that comprises a load region 34. The effort region 32 and the load region 34 can be rotated about the fulcrum 30 in response to application of force from the pump 10'. The container 14 can be progressively deformed or collapsed over time as the pump 10' applies force to the effort region 32. A skilled artisan will understand that, in some embodiments, the lever 12 can be used in place of the lever 12' in the substance delivery system 5, and the lever 12' can be used in place of the lever 12 in the substance delivery systems 1, 3. The lever 12' effort arm 12'a can have bends that allows to for increased lever advantage while decreasing a length of the substance delivery device 5. In other words, with bends in the effort arm 12'a, an effort distance d1 can be increased without increasing a foot print or lateral dimension of the substance delivery device 5.

In some applications the substance delivery system 5 can be designed to be used in a wearable device. In some embodiments, the substance delivery system 5 can be designed such that the substance delivery device 6 and the container 14 are packaged within a dimension of 40 millimeters (mm)×20 mm×10 mm (length×width×height).

In some applications, the substance delivery systems disclosed herein can be disposable and/or reusable. For example, the container 14 can be replaced once a week, once a day, or twice a day. For example, the substance delivery devices disclosed herein can be used over fourteen times with fourteen replacement of the container 14. For example, the substance delivery device 2, 4, 6 can be disposed after one week with about one to two replacements of the container 14 a day. In some embodiments, the substance delivery devices disclosed herein can be powered by a coin cell battery. In some embodiments, the substance delivery devices disclosed herein can operate with input voltage of 5 volts (V) or less.

In some embodiments, the substance delivery systems disclosed herein can deliver a substance from the reservoir 40 of the container 14 at a flow rate in a rage of, for example, 5 μm/min to 150 μm/min, in a rage of, for example, 5 μm/min to 100 μm/min, in a rage of, for example, 5 μm/min to 50 μm/min, in a rage of, for example, 50 μm/min to 150 μm/min, or in a rage of, for example, 50 μm/min to 100 μm/min. In some embodiments, the substance delivery system disclosed herein can have a delivery pressure at the access port 42, provided by any substance delivery device disclosed herein, up to about 15 pound per square inch (psi). In some embodiments the delivery pressure can be in a range from 5 psi to 15 psi.

Figure 6A:
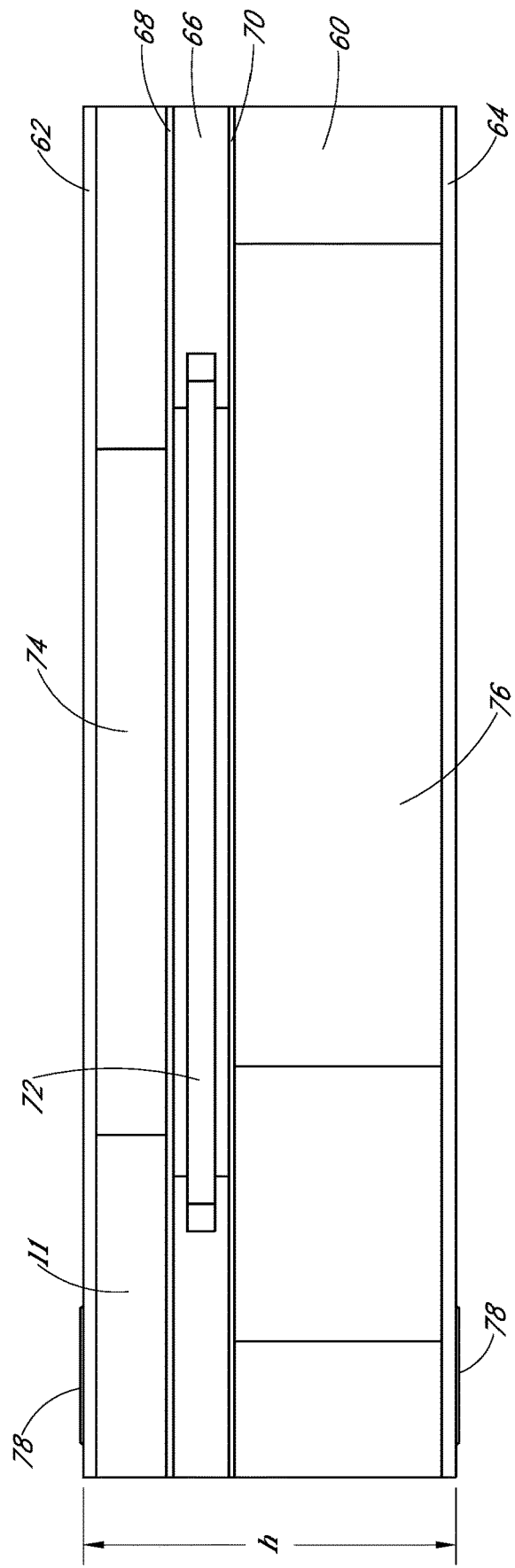
FIG. 6A is a schematic cross sectional side view of the pump illustrated in FIGS. 5A and 5B in the first state.
Figure 6B:
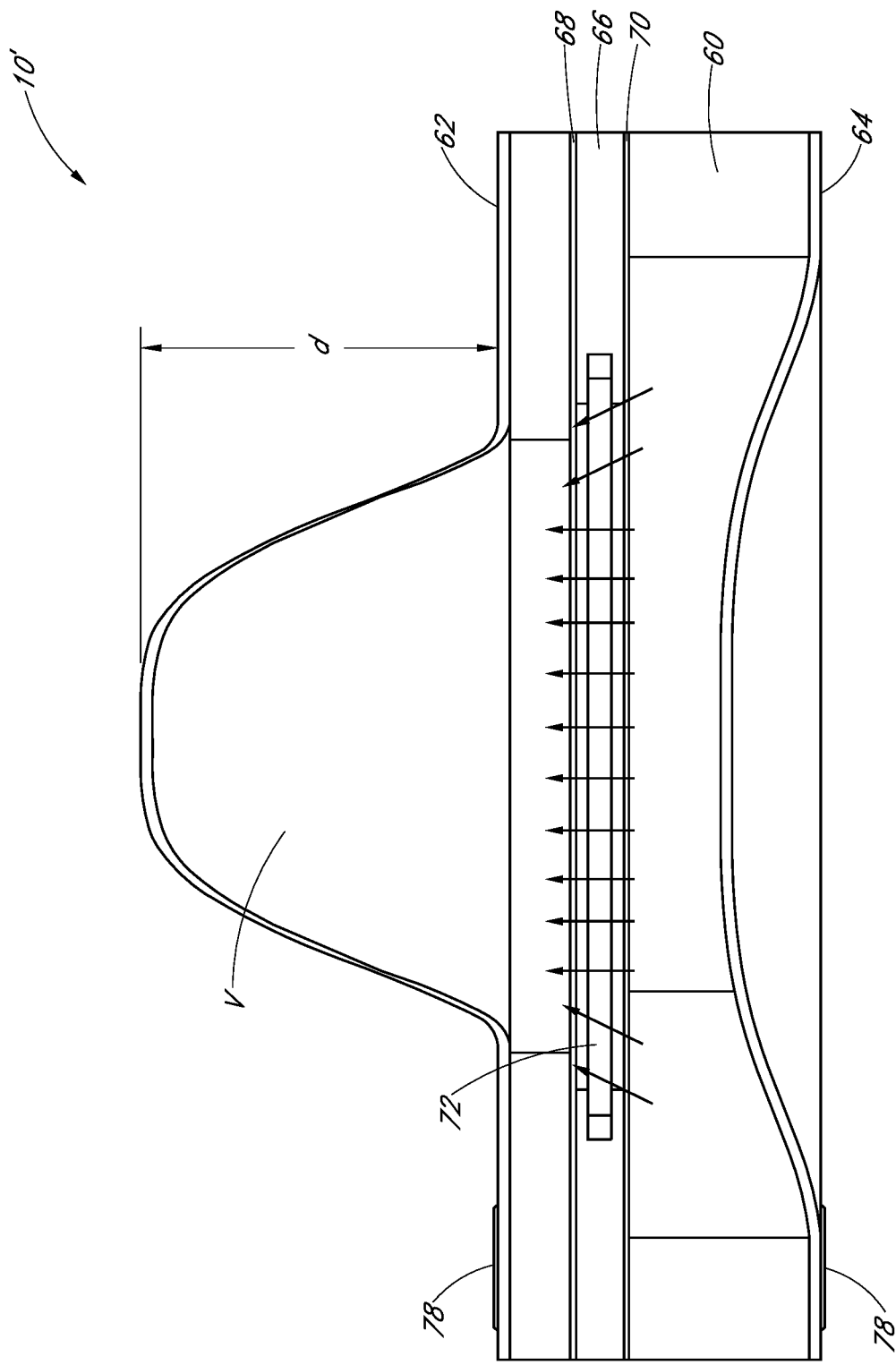
FIG. 6B is a schematic cross sectional side view of the pump illustrated in FIGS. 5A-6A in the second state.
Figure 7A:
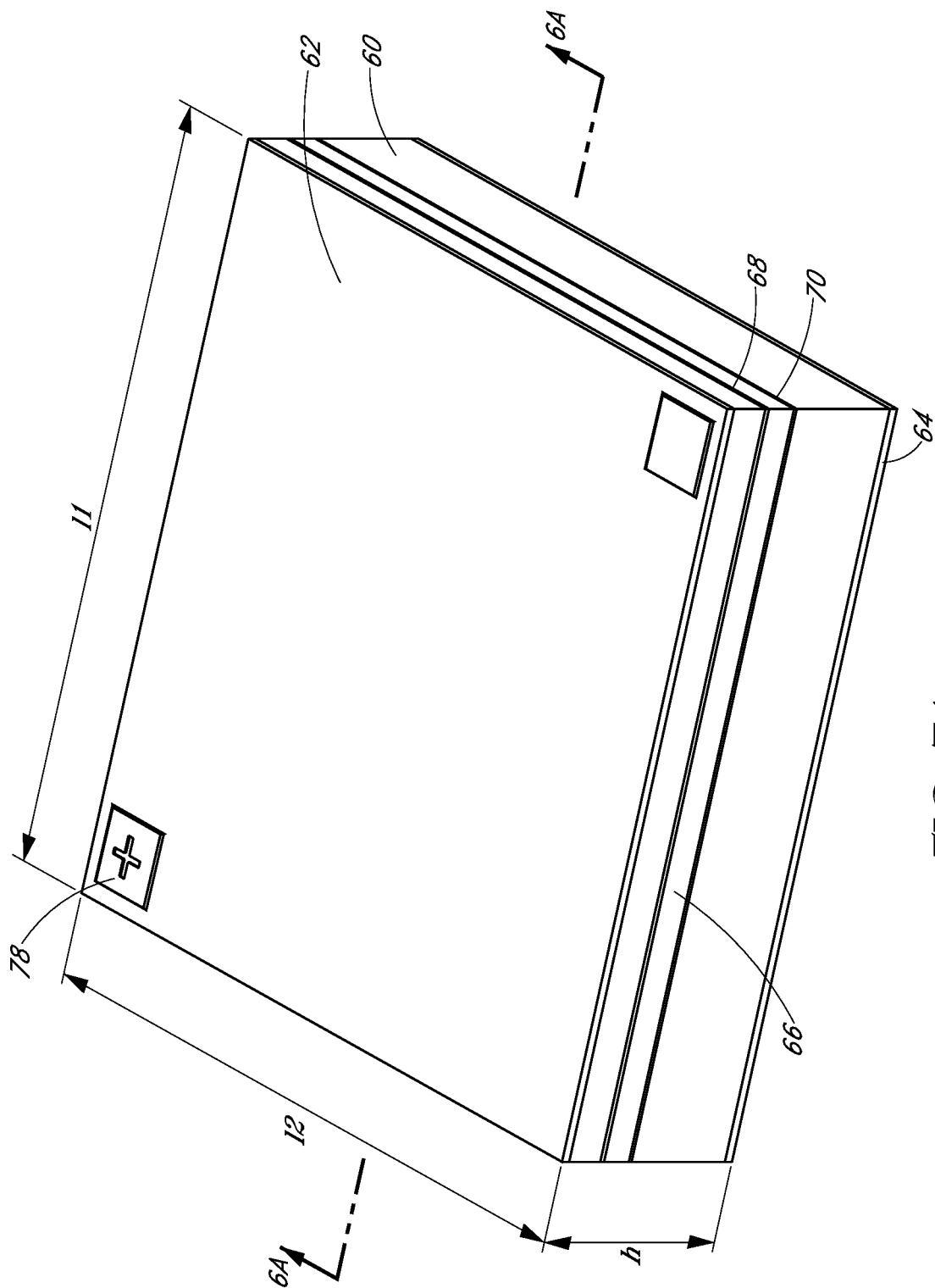
FIG. 7A is a schematic top perspective view of the pump of FIG. 6A.
Figure 7B:
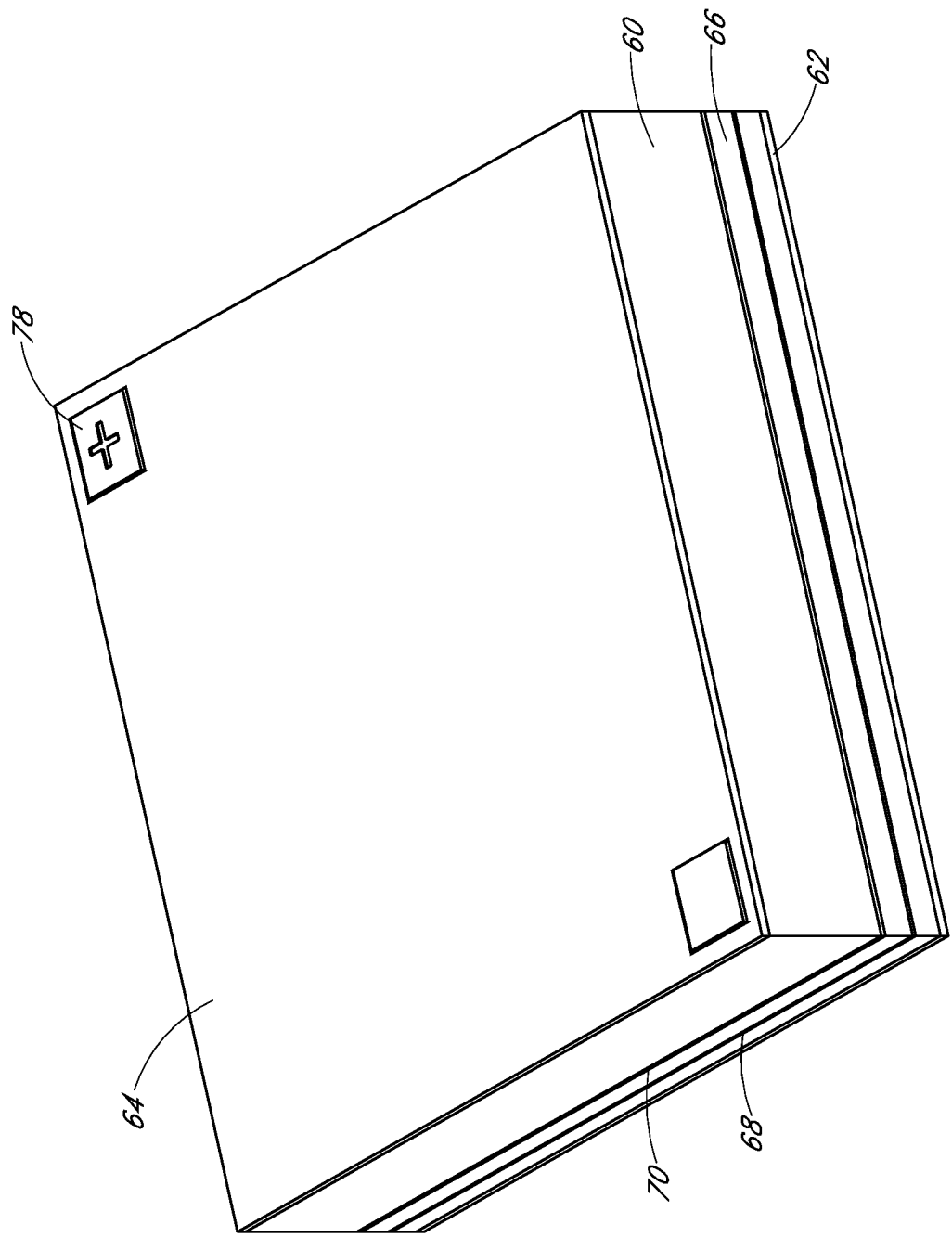
FIG. 7B is a schematic bottom perspective view of the pump of FIG. 6B.
Figure 7C:
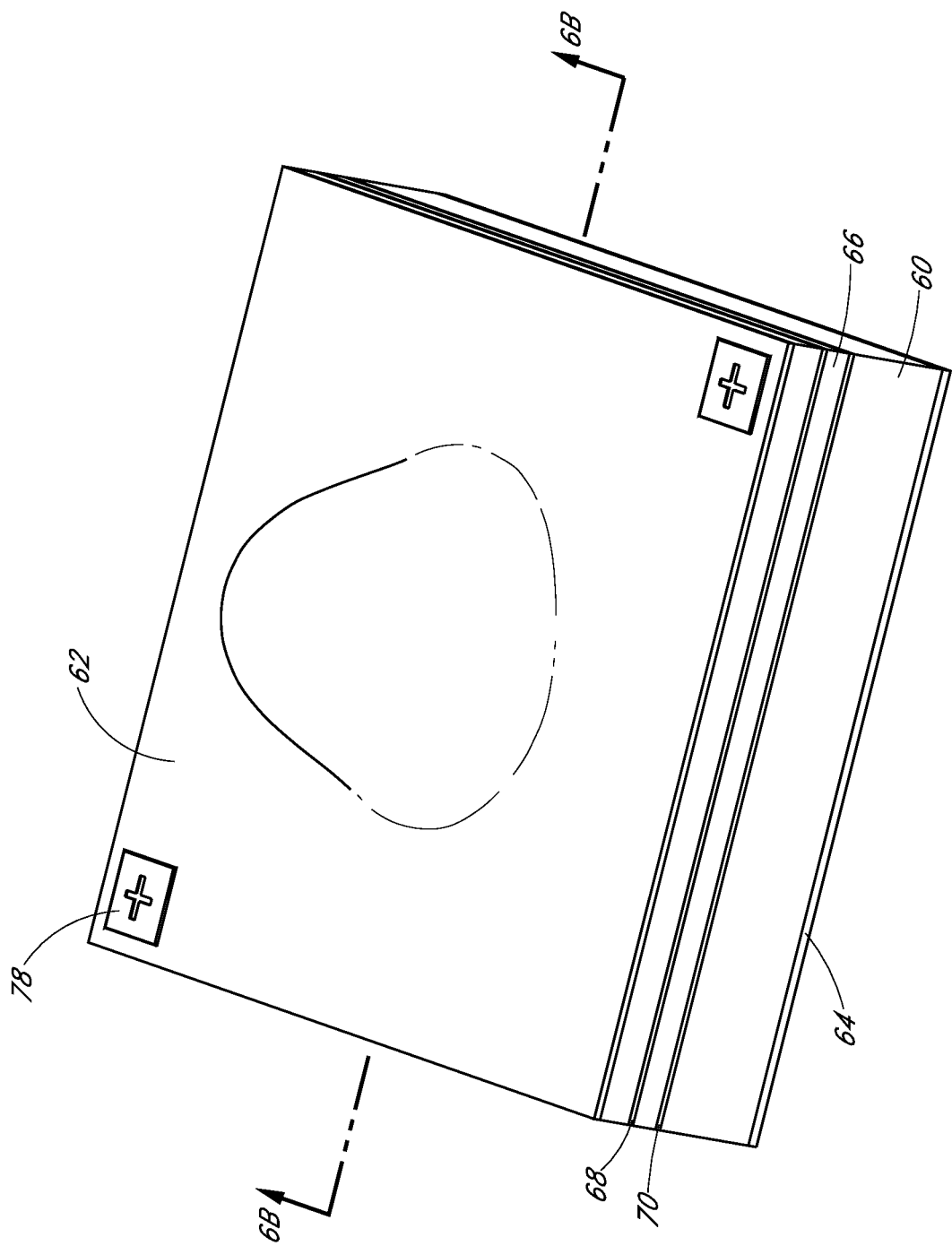
FIG. 7C is a schematic top perspective view of the pump of FIG. 6B.

FIG. 6A is a schematic cross sectional side view of the pump 10' illustrated in FIGS. 5A and 5B in a first state, according to one embodiment. FIG. 6B is a schematic cross sectional side view of the pump 10' illustrated in FIGS. 5A-6A in a second state. FIG. 7A is a schematic top perspective view of the pump 10' of FIG. 6A. FIG. 7B is a schematic bottom perspective view of the pump 10' of FIG. 6B. FIG. 7C is a schematic top perspective view of the pump 10' of FIG. 6B.

The pump 10' illustrated in FIGS. 6A-7C comprises an electroosmotic (EO) pump. The pump 10' can comprise a housing 60, a first elastic diaphragm 62 that is attached to a first side (an upper side) of the housing 60, a second elastic diaphragm 64 that is attached to a second side (lower side) of the housing 60, a spacer 66 that is positioned between the between the first side and the second side of the housing 60, a first electrode 68 that is positioned between the spacer 66 and the first elastic diaphragm 62, a second electrode 70 that is positioned between the spacer 66 and the second elastic diaphragm 64, and a porous membrane 72 positioned between the first electrode 68 and the second electrode 70. The pump 10' can include a first chamber 74 defined at least partially by the housing 60 and the first elastic diaphragm 62, and a second chamber 76 defined at least partially by the housing 60 and the second elastic diaphragm 64. The first chamber 74 and the second chamber 76 are configured to receive a solution (e.g. reverse osmosis (RO) water). At least portions of the spacer 66, first electrode 68, and the second electrode 70 can be positioned between the first chamber 74 and the second chamber 76. In some embodiments, the portions of the spacer 66, first electrode 68, and the second electrode 70 positioned between the first chamber 74 and the second chamber 76 can provide fluid communication between the first chamber 74 and the second chamber 76. The pump 10' can comprise contact pads 78 that can be electrically coupled to the first electrode 68 and the second electrode 70. In some embodiments, the contact pads 78 can be formed on or in a portion of the first elastic diaphragm 62 and or the second elastic diaphragm 64.

The first elastic diaphragm 62 and the second elastic diaphragm 64 can be sufficiently elastic so as to expand in response to an electroosmotic flow of a solution between the chambers 74, 76. In some embodiments, the expansions of the first elastic diaphragm 62 and the second elastic diaphragm 64 can maintain a pressure within the pump 10'. In other words, an internal pressure of the pump 10' in the first state can be the same or generally similar to the internal pressure of the pump 10' in the second state. For example, the second elastic diaphragm 64 can collapse inwardly and the first elastic diaphragm 62 can expand outwardly as shown. The inwardly collapsing second diaphragm 64 can avoid the generation of a vacuum in the chamber 76, thereby lowering the pressure differential used to create the same force on the lever 12. Therefore, the first chamber 74 and the second chamber 76 can comprise expandable or deformable chambers. The first elastic diaphragm 62 and the second elastic diaphragm 64 can comprise any suitable material. In some embodiments, the first elastic diaphragm 62 and/or the second elastic diaphragm 64 can comprise silicon rubber or high consistency rubber. In some embodiments, the first elastic diaphragm 62 and the second elastic diaphragm 64 can comprise the same material or different materials.

In some embodiments, the first electrode 68 and the second electrode 70 can comprise micro-pores (not illustrated). The micro-pores can allow the solution to flow across the first electrode 68 and the second electrode 70 (between the first chamber 74 and the second chamber 76). The micro-pores are large enough for the solution to go through but small enough for providing a sufficient magnetic field during operation of the substance delivery device 5. In some embodiments, a side of the micro-pore of the first electrode 68 and the second electrode 70 can be less than about 10 μm. In some embodiments, there can be a gap (not illustrated) between the first electrode 68 and the porous membrane 72. Likewise, there can be a gap (not illustrated) between the first electrode 68 and the porous membrane 72. In some embodiments, the gap can be provided by the spacer 66. In some embodiments, the gap can be in a range from 20 μm to 30 μm. The gap can be about 25 μm in some embodiments. In some applications, the gap can facilitate fluid flow from between the first chamber 74 and the second chamber 76. For example, absent the gap, it may be less efficient for the solution to go through the porous membrane 72 and the first electrode 68 and the second electrode 70 than with the gap. The gap can be sufficiently narrow such that the voltage applied to the first electrode 68 and the second electrode 70 can create a desired electroosmosis reaction.

The porous membrane 72 can comprise any suitable material. In some embodiments, the porous membrane 72 can comprise silicon, glass aluminum, or polymer. The porous membrane 72 can comprise pores. In some embodiments, a size of the pore of the porous membrane 72 can be in a range from, for example, 100 nanometer (nm) to 200 nm, in a range from, for example, 100 nm to 150 nm, or in a range from, for example, 150 nm to 200 nm. In some embodiments, the pores of the porous membrane 72 have a porosity in a range from, for example, 40% to 60%, in a range from, for example, 50% to 60%, or in a range from, for example, 40% to 50%.

The pump 10' has a height h, lengths l1, l2 in a direction perpendicular to the height. In the illustrated embodiment, the length l1, l2 of the pump 10' are the same. However, in some other embodiments, the lengths l1, l2 can be different. In some embodiments, the height h of the pump 10' can be smaller than about 3 mm. In some embodiments, the height h of the pump 10' can be in a range of, for example, 1 mm to 3 mm, in a range of, for example, 2 mm to 3 mm, or in a range of, for example, 2.5 mm to 3 mm. In some embodiments, an area formed by the length l1, l2 can be less than about 100 mm². In some embodiments, the length l1, l2 of the pump 10' can be about 10 mm. In some embodiments, the length l1, l2 of the pump 10' can be in a range of, for example, 5 mm to 15 mm, in a range of, for example, 5 mm to 10 mm, or in a range of, for example, 8 mm to 12 mm. In some applications, having the dimension of the pump 10' relatively small can be beneficial. In such pump 10' with small dimension can require relatively low power to operate and provide relatively fast response time for an electroosmosis reaction.

An example operation of the pump 10' will be described with reference to FIGS. 6A-7C. In the first state illustrated in FIGS. 6A and 7A, the solution in the pump 10' can be in an equilibrium state. For example, in some embodiments, in the first state, no external power (voltage) may be applied to the first electrode 68 and the second electrode 70. In the first state, no electroosmotic flow is created from the second chamber 76 to the first chamber 74 (or vice versa). In the first state, the first elastic diaphragm 62 and the second elastic diaphragm 64 can be relaxed.

In the second state illustrated in FIGS. 6B, 7B and 7C, electrical power (voltage) is applied to the first electrode 68 and the second electrode 70. The second state is referred to a state in which at least some external force that is sufficient enough to at least partially deform or collapse the container 14 is applied by the pump 10'. In the second state, a pressure difference between the first chamber 74 and the second chamber 76 created by the applied voltage can create an electroosmotic flow of the solution from the second chamber 76, through the porous membrane 72, and into the first chamber 74. The electroosmotic flow in the second state is shown with arrows in FIG. 6B. The electroosmotic flow can be controlled by controlling the applied voltage. In some embodiments, a coin cell battery can provide the voltage. In some embodiments, the pump 10' can operate with applied voltage of less than about 5V.

Referring to FIG. 6B, the first elastic diaphragm 62 can protrude from the housing 60 in response to the electroosmotic flow of the solution. The protruded portion of the first elastic diaphragm 62 has a displacement d and a volume v. The displacement d and the volume v can be interrelated. The displacement d and the volume v can be controlled by changing the voltage applied to the first electrode 68 and the second electrode 70. For Example, when a lower voltage is applied, the displacement d and the volume v can be smaller than when a higher voltage is applied. By controlling the applied voltage, the displacement d and the volume v can be controlled. In some embodiments, a maximum value of the volume v can be in a range of, for example, 25 μL to 100 μL, in a range of, for example, 25 μL to 75 μL, or in a range of, for example, 50 μL to 75 μL.

Figure 8:
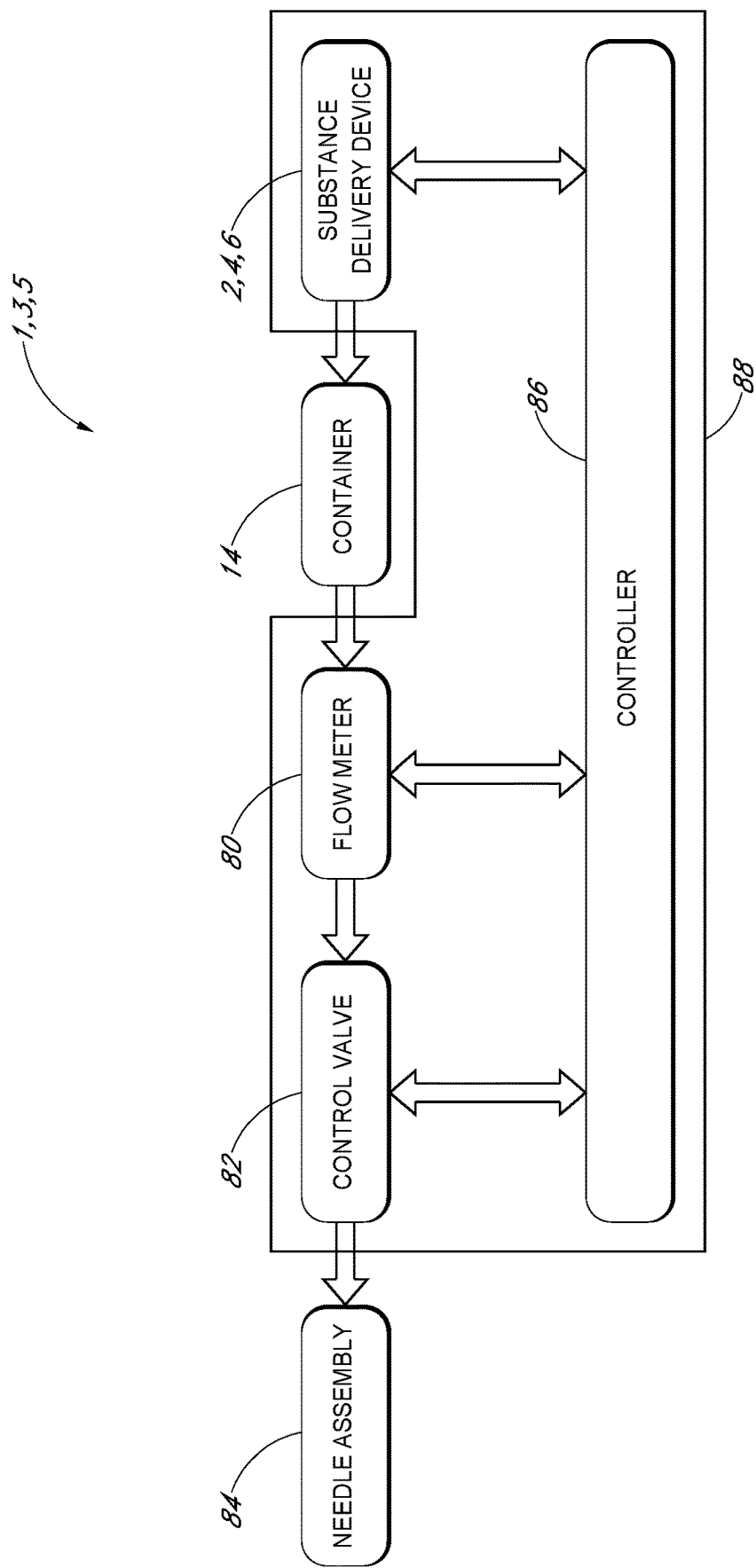
FIG. 8 is a block diagram of a substance delivery system according to one embodiment.

FIG. 8 is a block diagram of a substance delivery system 1, 3, 5, according to one embodiment. The substance delivery system 1, 3, 5 can include a substance delivery device, 2, 4, 6, a container 14, a flow meter 80, a control valve 82, a needle assembly 84, and a controller 86. In some embodiments, the substance delivery device, 2, 4, 6, the flow meter 80, the control valve 82, and the controller 86 can define a substance delivery module 88. In some embodiments, the control valve 82 may be positioned between the substance delivery device, 2, 4, 6 and the flow meter 80.

The flow meter 80 can monitor a flow rate and a flow amount of the substance flowing through the flow meter 80 from the container 14. The control valve 82 can prevent or mitigate a backflow of the substance. In some embodiments, the control valve 82 can open/close to stop/allow the substance flow. The controller 86 can control operation of the substance delivery module 88. The controller 86 can include processing electronics that are programmed to control operation of the substance delivery system 1, 3, 5. The controller 86 can include one or more processors, one or more memory devices, etc. For example, the substance delivery device 2, 4, 6, the flow meter 80, and the control valve 82 can connect to the controller 86 and be controlled by the controller 86. In some embodiments, the substance delivery device 2, 4, 6, the flow meter 80, and the control valve 82 can be connected with the controller 86 through a wired connection or wirelessly (e.g., through an electromagnetic wave). In some embodiments, the controller 86 a user interface (including, e.g., buttons, displays, etc.) that can allow a user to control the substance delivery module 88, or to monitor the activities of the substance delivery module 88. In some embodiments, the controller 86 can be connected to other sensors, such as an accelerometer, thermometer, etc. In some embodiments, the controller 86 can be connected to a vital sign monitoring device. In some embodiments, the controller 86 can be programmed to deliver certain amount of a substance (e.g., a drug) to a target location over time. For example, the controller 86 can be programmed such that after a time period T(x), a voltage V(x) is applied across the first electrode 68 and the second electrode 70. In response to the voltage V(x) applied, the elastic displacement d and the volume v can be increased/decreased, depending on the desired dosage to be delivered to the patient at a particular time.

In some applications, the flow meter 80 can monitor a substance flow to measure a delivered volume of the substance, a flow rate, and/or a flow direction (e.g., forward flow or backflow). The measured data can be compared against a predetermined or prescribed dosage of the substance. The measured data can be used to regulate the voltage on the pump 10'. The measured data can be used to operate, for example, the control valve (e.g., a shutoff valve or check valve).

The needle assembly 84 can comprise a conduit (e.g., a tube) and a needle that is coupled to the conduit. In some applications, the needle can be inserted into a patient's body through the skin such that the fluid substance (e.g., drug) delivered from the container by the substance delivery module 88 is conveyed to an interior of the patient (e.g., the patient's vascular system) through the needle assembly 88.

Although disclosed in the context of certain embodiments and examples, it will be understood by those skilled in the art that the present invention extends beyond the specifically disclosed embodiments to other alternative embodiments and/or uses and obvious modifications and equivalents thereof. In addition, while several variations have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the present disclosure. It should be understood that various features and aspects of the disclosed embodiments can be combined with, or substituted for, one another in order to form varying modes of the disclosed invention. Thus, it is intended that the scope of the present invention herein disclosed should not be limited by the particular disclosed embodiments described above, but should be determined only by a fair reading of the aspects that follow.

What is claimed is:

1. A substance delivery device comprising:
a lever comprising a drive arm rotatable about a pivot; and
an electroosmotic (EO) pump having a deformable chamber, the deformable chamber configured to rotate the drive arm about the pivot towards a container so as to deform the container to drive a fluid substance from the container;
wherein the EO pump is configured to apply an effort force to an effort region of the lever, thereby causing the effort region and a load region of the lever to move, the load region positioned to apply a load force to the container; and
wherein the drive arm comprises a load region and an effort region, the effort region is positioned between the load region and the pivot.

2. The device of claim 1, wherein the EO pump and the lever are arranged such that an expansion volume of the deformable chamber is smaller than a volume of the fluid substance driven.

3. The device of claim 2, wherein the volume of the fluid substance is at least twice the expansion volume.

4. The device of claim 2, wherein the expansion volume is 25 micro liters (μL) to 100 μL.

5. The device of claim 1, further comprising a package substrate having one or more electrical interconnections, the lever and the EO pump are electrically coupled to the package substrate.

6. A substance delivery system comprising:
the substance delivery device of claim 1 coupled to a support; and
the substance container coupled to the support, the substance delivery system and the substance container being coupled to a same side of the support.

7. A substance delivery device comprising:
a lever having a fulcrum, an effort region, and a load region; and
an electroosmotic (EO) pump having a deformable chamber, the EO pump configured to apply an effort force to the effort region of the lever thereby causing the effort region and the load region of the lever to move, the load region positioned to apply a load force to a container that includes a fluid substance;
wherein the lever comprises a drive arm that extends from the fulcrum, the drive arm comprises the load region, the drive arm comprises the effort region, the effort region is positioned between the load region and the fulcrum.

8. The device of claim 7, wherein the EO pump further comprises a second deformable chamber, a porous electrode positioned between the deformable chamber and the second chamber, and a porous membrane positioned between the deformable chamber and the second chamber, the deformable chamber and the second deformable chamber are in fluid communication.

9. The device of claim 7, wherein the EO pump and the lever are arranged such that an amplified displacement of the lever at the load region in response to the application of the effort force is greater than a displacement of the lever at the effort region in response to the application of the effort force.

10. The device of claim 9, wherein the amplified displacement of the lever at the load region is at least twice the displacement of the lever at the effort region.

11. The device of claim 7, wherein the EO pump causes the deformable chamber to expand by between about 25 micro liters (pL) and 100 pL.

12. The device of claim 7, further comprising a package substrate having electrical interconnects, the lever and the EO pump are electrically coupled to the package substrate.

13. A substance delivery device comprising:
- a lever having a fulcrum, an effort region, and a load region, the lever coupled to a substrate; and
- an electroosmotic (EO) pump configured to apply an effort force to the effort region of the lever to cause the effort region and the load region of the lever to move, the load region positioned to apply a load force to a container that includes a fluid substance to drive the fluid substance from the container;
- wherein the EO pump and the lever are arranged such that an amplified displacement of the lever at the load region in response to the application of the force is greater than a displacement of the lever at the effort region in response to the application of the force.

14. The device of claim 13, wherein the EO pump comprises a deformable chamber, the deformable chamber configured to deform and apply the effort force to the effort region of the lever.

15. The device of claim 13, wherein the amplified displacement is at least twice the displacement.

\* \* \* \* \*